(12) United States Patent
Chan

(10) Patent No.: US 8,428,337 B2
(45) Date of Patent: *Apr. 23, 2013

(54) APPARATUS FOR DETECTING MICRO-CRACKS IN WAFERS AND METHOD THEREFOR

(75) Inventor: Sok Leng Chan, Singapore (SG)

(73) Assignee: Bluplanet Pte Ltd, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/681,722

(22) PCT Filed: May 15, 2009

(86) PCT No.: PCT/SG2009/000174
§ 371 (c)(1),
(2), (4) Date: Apr. 5, 2010

(87) PCT Pub. No.: WO2010/062262
PCT Pub. Date: Jun. 3, 2010

(65) Prior Publication Data
US 2011/0268344 A1    Nov. 3, 2011

(30) Foreign Application Priority Data
Nov. 25, 2008    (SG) .................................. 200808731

(51) Int. Cl.
*G06K 9/00*    (2006.01)

(52) U.S. Cl.
USPC ...................... 382/145; 356/237.1; 356/237.6

(58) Field of Classification Search .... 356/237.1–237.5; 382/145
See application file for complete search history.

(56) References Cited

U.S. PATENT DOCUMENTS 6,088,470 A    7/2000 Camus et al.
6,829,047 B2    12/2004 Fujii et al.
(Continued)

FOREIGN PATENT DOCUMENTS

JP    2003-017536 A    1/2003
JP    2004-317470 A    11/2004
(Continued)

OTHER PUBLICATIONS

International Search Report dated Dec. 21, 2009 in foreign application (PCT/SG2009/000173).
International Search Report dated Dec. 7, 2009 in corresponding foreign application (PCT/SG2009/000174).
(Continued)

*Primary Examiner* — Tarifur Chowdhury
*Assistant Examiner* — Isiaka Akanbi
(74) *Attorney, Agent, or Firm* — Nields, Lemack & Frame, LLC

(57) ABSTRACT

A method and apparatus for wafer inspection is disclosed. The method and apparatus involve directing light substantially along a first axis towards a first surface of a wafer to thereby obtain light emanating along the first axis from a second surface of the wafer, wherein the first and second surfaces of the wafer are substantially outwardly opposing and substantially extending parallel to a plane. The method and apparatus further involve directing light substantially along a second axis towards the first surface of the wafer to thereby obtain light emanating along the second axis from the second surface of the wafer, the first axis being angled away from the second axis about a reference axis extending along the plane. More specifically, the orthographic projection of the first axis on the plane is substantially parallel to the orthographic projection of the second axis on the plane, and each the orthographic projections of the first and second axes on the plane is substantially orthogonal to the reference axis.

20 Claims, 7 Drawing Sheets

U.S. PATENT DOCUMENTS

| | | | |
|---|---|---|---|
| 6,891,570 B2 | 5/2005 | Tantalo et al. | |
| 7,283,224 B1 * | 10/2007 | Smithgall | 356/237.1 |
| 7,667,834 B2 * | 2/2010 | Clasen | 356/237.1 |
| 7,801,357 B2 | 9/2010 | Yoshiura et al. | |
| 8,077,305 B2 * | 12/2011 | Owen et al. | 356/237.1 |
| 8,149,376 B2 * | 4/2012 | Ohashi | 349/192 |
| 2006/0278831 A1 | 12/2006 | Matsumoto et al. | |
| 2007/0009148 A1 | 1/2007 | Brasen et al. | |
| 2007/0188610 A1 | 8/2007 | Micotto et al. | |
| 2007/0262002 A1 * | 11/2007 | Ito et al. | 209/580 |
| 2007/0263206 A1 * | 11/2007 | LeBlanc et al. | 356/239.7 |
| 2010/0177191 A1 * | 7/2010 | Stier | 348/92 |
| 2010/0220186 A1 | 9/2010 | Chan | |
| 2011/0268344 A1 * | 11/2011 | Chan | 382/145 |

FOREIGN PATENT DOCUMENTS

| | | |
|---|---|---|
| JP | 2007-147547 A | 6/2007 |
| JP | 2007-218638 A | 8/2007 |
| JP | 2008-267851 A | 11/2008 |
| KR | 10-1994-0020481 A | 9/1994 |
| WO | 2005/100961 | 10/2005 |
| WO | 2007/041758 | 11/2007 |

OTHER PUBLICATIONS

Office Action-Restriction—mailed Aug. 27, 2012 in co-pending U.S. Appl. No. 12/681,717.

Office Action mailed Dec. 3, 2012 in co-pending U.S. Appl. No. 12/681,717.

* cited by examiner

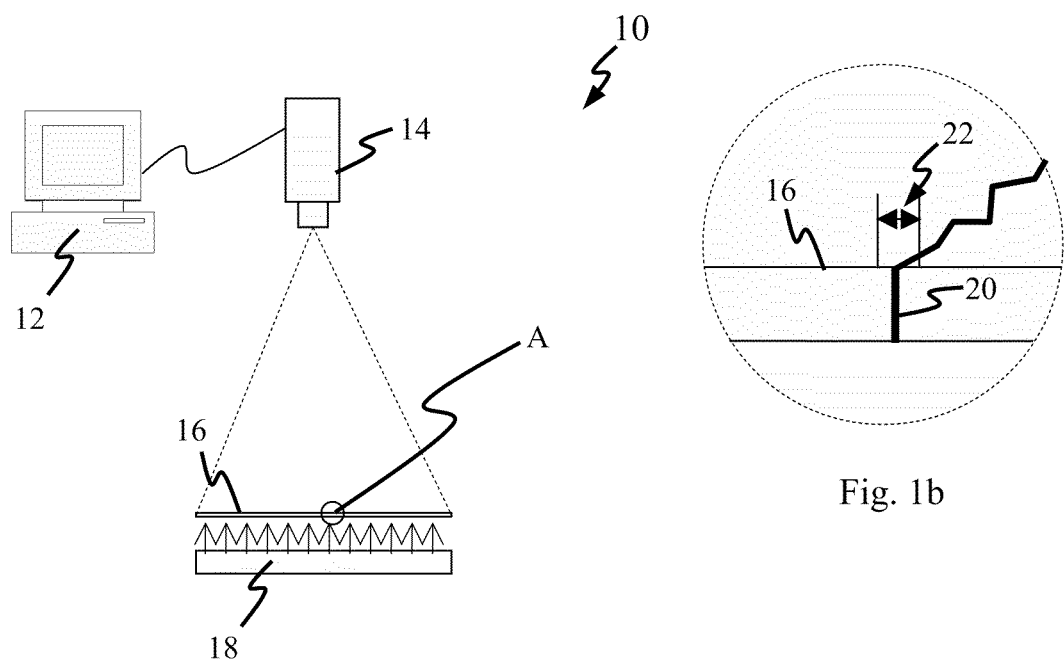
Fig. 1a
Fig. 1b
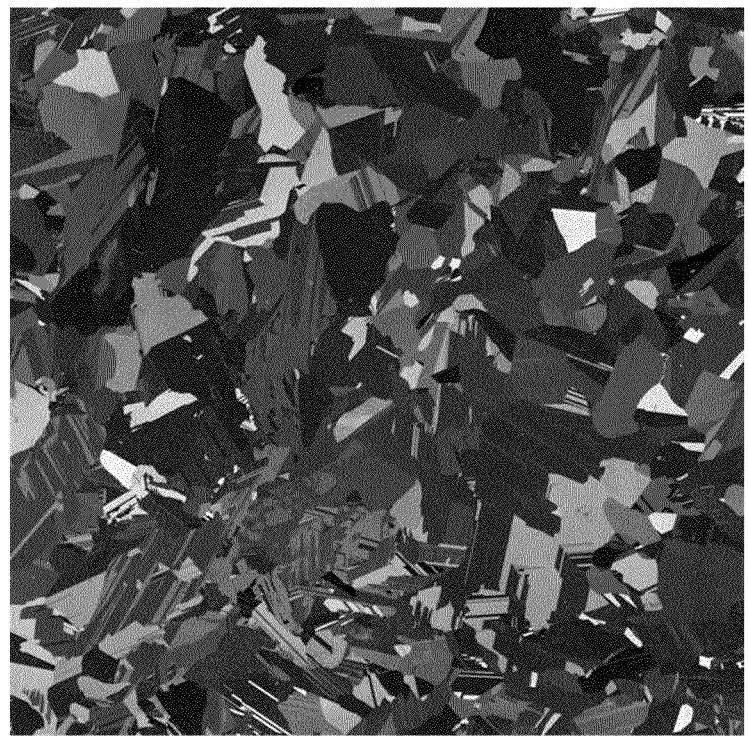
Fig. 2

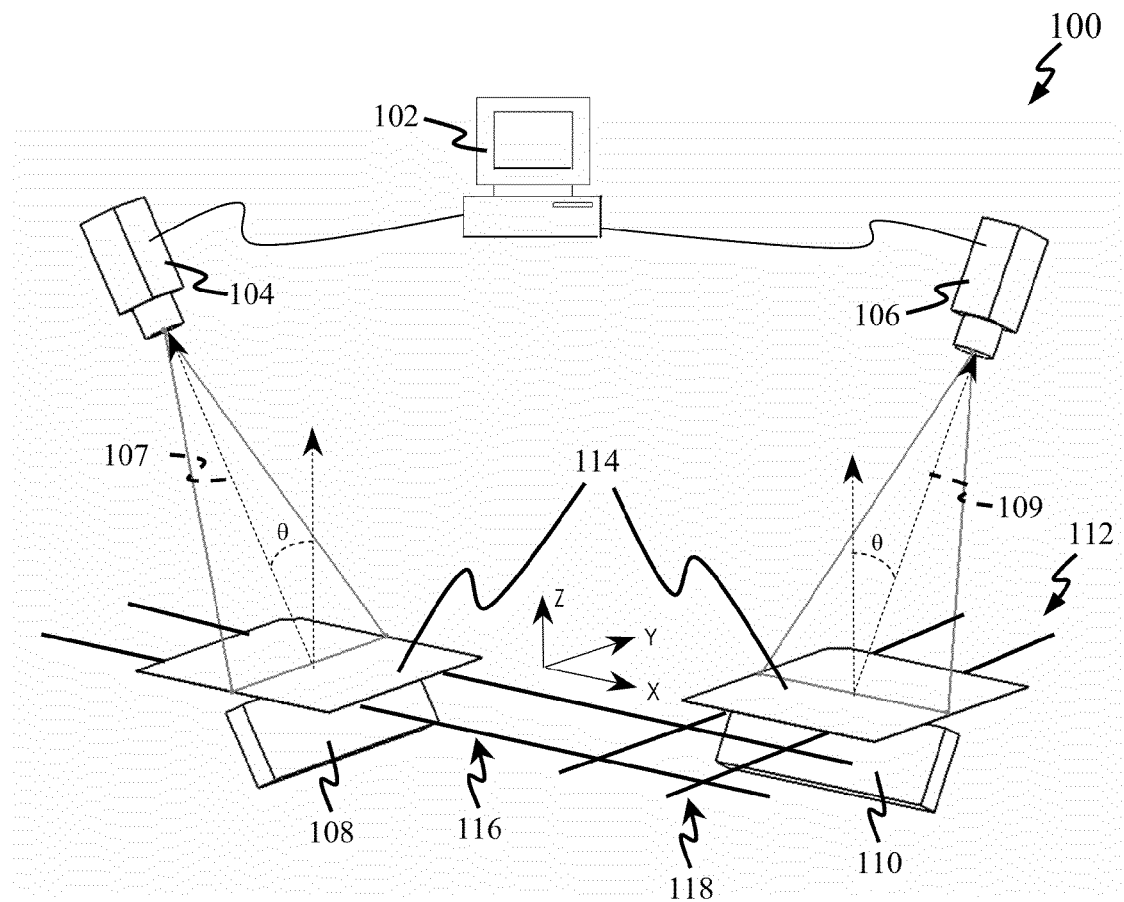
Fig. 4
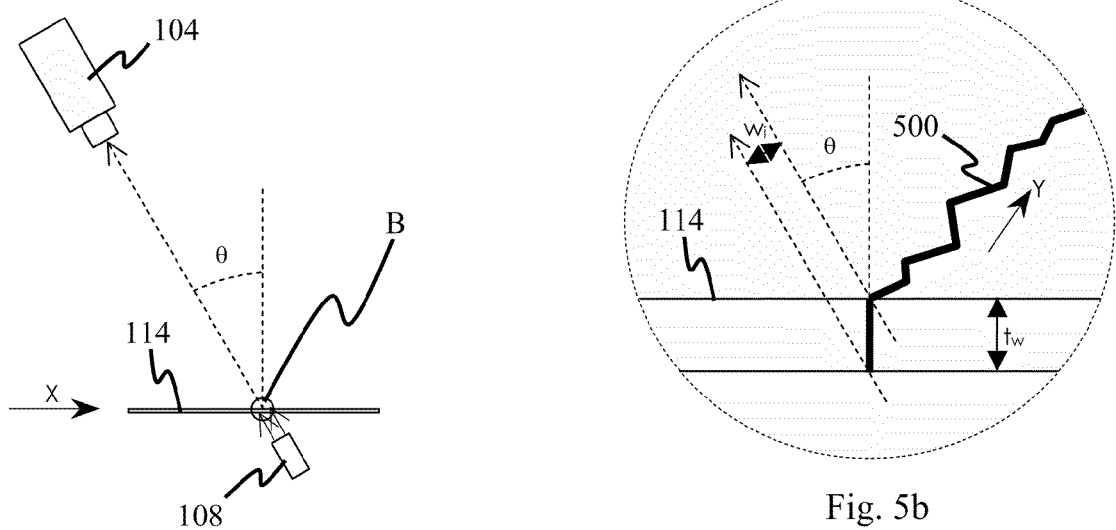
Fig. 5a
Fig. 5b

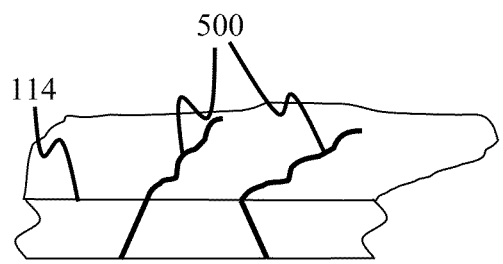
Fig. 5c
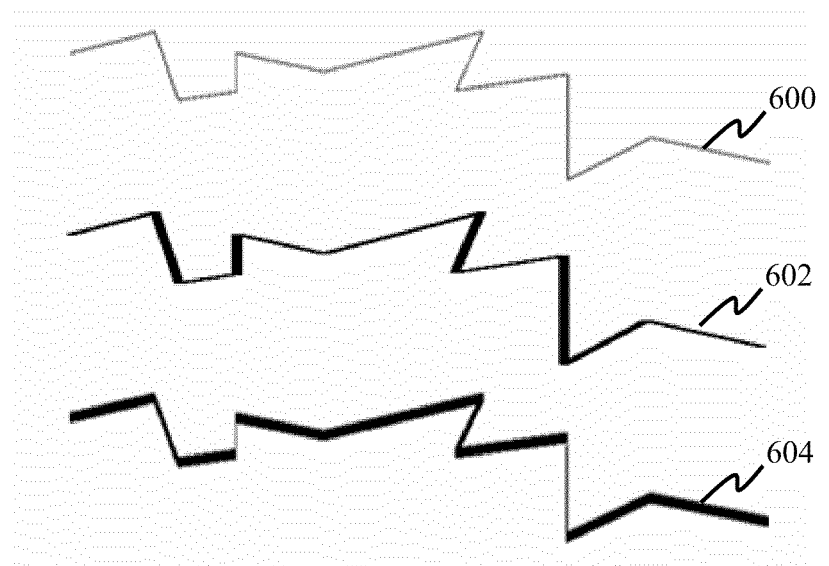
Fig. 6a
Fig. 6b
Fig. 6c

APPARATUS FOR DETECTING MICRO-CRACKS IN WAFERS AND METHOD THEREFOR

FIELD OF INVENTION

The present invention generally relates to for inspection of an object. In particular, the invention relates to an apparatus and a method for inspecting wafers for defects.

BACKGROUND

Solar cells manufacturers routinely perform inspection on their solar wafers. This is to ensure that any defective solar wafers are identified so as to control the quality of the solar cells.

A solar wafer is a thin slice of silicon crystal that is commonly used in the fabrication of solar cells. A solar wafer serves as a substrate for solar cells and undergoes a series of fabrication processes, for example deposition, etching and patterning, before becoming a functional solar cell. It is therefore very critical to maintain the quality of solar wafers from the beginning of the fabrication processes in order to improve production yield and reduce production cost.

Micro-cracks are common defects found in solar wafers, which is extremely difficult to detect because some micro-cracks are invisible to the human eyes and even to optical microscopes. One method of detecting micro-cracks in solar wafers involves the use of infrared imaging technique. Solar wafers are made from silicon of high purity and appear opaque under visible light. However, due to silicon's bandgap energy level, solar wafers appear transparent when illuminated with light having a wavelength larger than 1127 nm.

Light having a wavelength of 1127 nm is classified as near infrared (NIR) radiation. NIR is invisible to the human eye but is detectable by most commercial CCD or CMOS infrared cameras. Examples of infrared light sources are Light Emitting Diodes (LED), tungsten lamp and halogen lamp.

As infrared light is capable of penetrating through a solar wafer made from silicon, it is possible to examine the internal structure of the solar wafer by displacing the solar wafer in between the infrared camera and light source.

Solar wafers are manufactured in a production line at high volume, typically at a rate of one wafer per second. A solar wafer typically has a rectilinear shape and a surface dimension of between 100 mm by 100 mm and 210 mm by 210 mm. The solar wafer also has a typical thickness of between 150 µm to 250 µm. A conventional high speed imaging system is used for inspecting the solar wafers. Most conventional high speed imaging system uses a line-scan CCD/CMOS camera that has a resolution of up to 12000 (12K) pixels.

FIG. 1a shows a conventional high speed imaging system 10. The conventional high speed imaging system 10 consists of a computer 12 and a line-scan imaging device 14. The line-scan imaging device 14 includes cameras and a lens system and is positioned above a solar wafer 16 perpendicularly to its surface. An infrared light source 18 is placed below the solar wafer 16 such that infrared light penetrates the solar wafer 16 and reaches the line-scan imaging device 14.

To inspect a 210 mm by 210 mm solar wafer, a 12K line-scan camera is required to have an image resolution better than 210 mm/12,000pixels or 18 µm/pixel. Based on sampling theorem, this image resolution is only useful for detecting micro-cracks having a crack line width of more than 2 pixels. This means that conventional high speed imaging systems are limited to detecting micro-cracks that has a crack line width larger than 2 pixels×18 µm/pixel or 36 µm. This is a major limitation to conventional high speed imaging systems because the width of micro-cracks is typically smaller than 36 µm.

FIG. 1b shows a close-up view of a micro-crack 20 along a cross-section of the solar wafer 16 at point A of FIG. 1a. The micro-crack 20 has a width smaller than the image resolution 22 of the conventional high speed imaging system 10. As a result, output images of the micro-crack 20 do not have sufficient contrast to allow image analysis software to detect the micro-crack 20.

Other than the image resolution problem, detecting micro-crack in solar wafers becomes more complicated when the solar wafer is of multi-crystalline type. Solar wafers are typically fabricated from mono-crystalline or multi-crystalline wafers. Mono-crystalline solar wafers are typically made by cutting single-crystal silicon into slices. Multi-crystalline solar wafers, on the other hand, are obtained by melting a pot of silicon and then allowed the melted silicon to cool slowly before cutting the solidified silicon into slices. Although multi-crystalline solar wafers are lower in quality than mono-crystalline solar wafers due to higher impurity level in the silicon, multi-crystalline solar wafers are nonetheless more cost effective and are becoming more widely used than mono-crystalline solar wafer for making solar cells. Mono-crystalline solar wafers appear to have a uniform surface texture. As shown in FIG. 2, multi-crystalline solar wafers exhibit complicated random surface texture due to the formation of crystal grains of varied size during the solidification process.

The random surface texture in multi-crystalline solar wafers also appears in the output images of the conventional high speed imaging systems 10. Crystal grain boundaries and the contrast between different crystal grains increase the difficulty in detecting the micro-cracks.

There is therefore a need for an improved method and system for facilitating detection of micro-cracks in wafers.

SUMMARY

Embodiments of the invention disclosed herein involve an improved system and method for facilitating detection of micro-cracks in wafers.

Therefore, in accordance with a first aspect of the invention, there is disclosed a method for wafer inspection. The method comprises directing light substantially along a first axis towards a first surface of a wafer to thereby obtain light emanating along the first axis from a second surface of the wafer, wherein the first and second surfaces of the wafer are substantially outwardly opposing and substantially extending parallel to a plane. The method further comprises directing light substantially along a second axis towards the first surface of the wafer to thereby obtain light emanating along the second axis from the second surface of the wafer, the first axis being angled away from the second axis about a reference axis extending along the plane. More specifically, the orthographic projection of the first axis on the plane is substantially parallel to the orthographic projection of the second axis on the plane, and each of the orthographic projections of the first and second axes on the plane is substantially orthogonal to the reference axis.

In accordance with a second aspect of the invention, there is disclosed an apparatus comprising a first light source that directs light substantially along a first axis towards a first surface of a wafer to thereby obtain light emanating along the first axis from a second surface of the wafer, wherein the first and second surfaces of the wafer are substantially outwardly opposing and substantially extending parallel to a plane. The apparatus further comprises a second light source that directs light substantially along a second axis towards the first surface of the wafer to thereby obtain light emanating along the second axis from the second surface of the wafer, the first axis being angled away from the second axis about a reference axis extending along the plane. More specifically, the orthographic projection of the first axis on the plane is substantially parallel to the orthographic projection of the second axis on the plane, and each of the orthographic projections of the first and second axes on the plane is substantially orthogonal to the reference axis.

BRIEF DESCRIPTION OF THE DRAWINGS

Embodiments of the invention are disclosed hereinafter with reference to the drawings, in which:

FIG. 1a shows a conventional system for inspecting a solar wafer and FIG. 1b is an enlarged cross-sectional view of the solar wafer;

FIG. 2 shows a multi-crystalline structure of a solar wafer;

FIG. 4 is an inspection apparatus according to a second embodiment of the invention;

FIG. 5a is a side view of the apparatus of FIG. 4 along the x-axis, FIG. 5b is an enlarged cross-sectional view of a solar wafer and FIG. 5c is a perspective view of the solar wafer showing non-vertical micro-cracks;

FIGS. 6a to 6c are images of micro-cracks obtained by the apparatus of FIG. 4;

DETAILED DESCRIPTION

Figure 3:
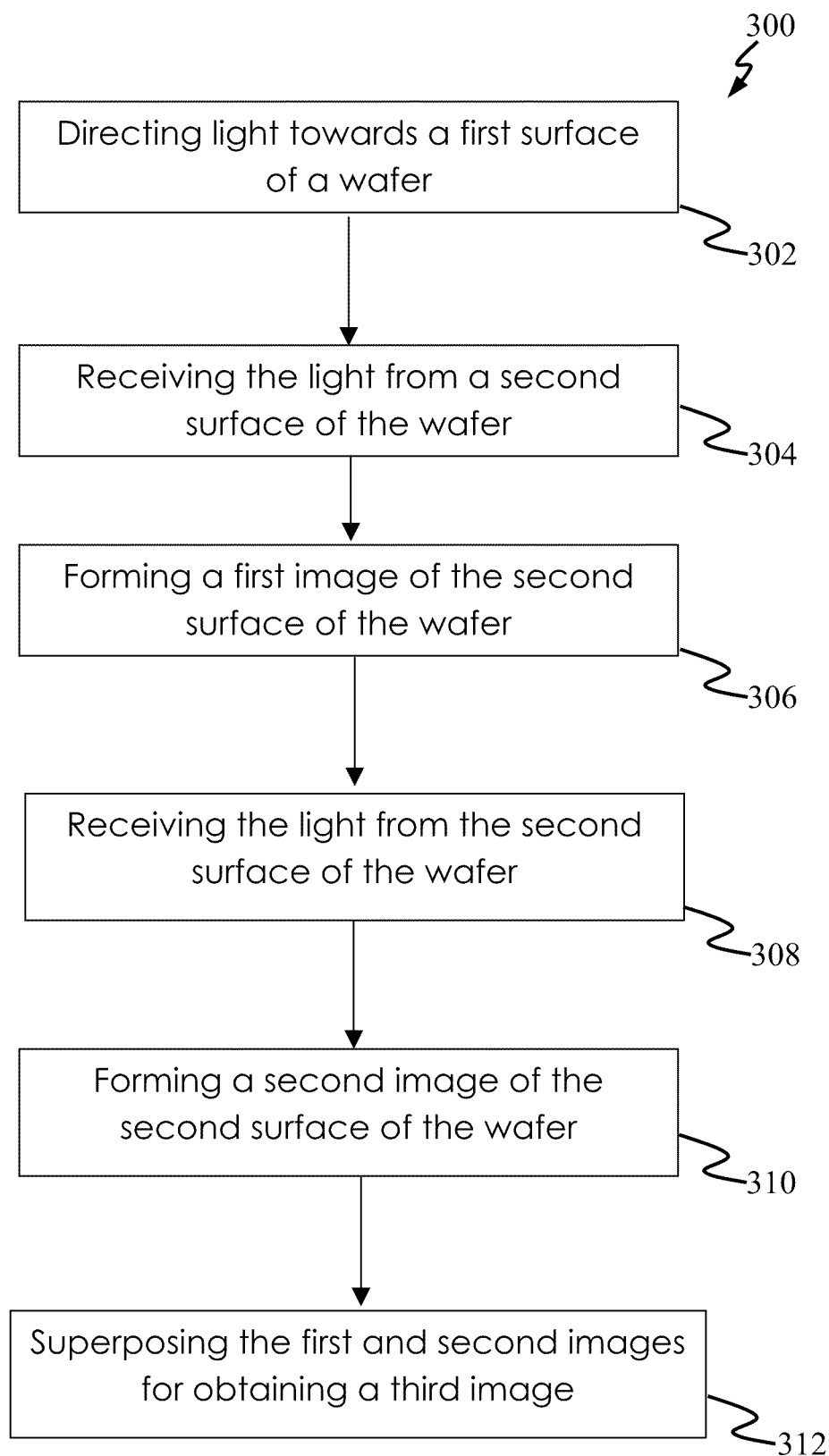
FIG. 3 is an inspection method according to a first embodiment of the invention.

With reference to the drawings, embodiments of the invention described hereinafter relate to creating a high contrast image of solar wafers for inspection purposes to facilitate detection of micro-cracks thereon.

Conventional methods and systems of creating images of solar wafers do not produce an image that has sufficiently high contrast for detecting minute micro-cracks on the solar wafers. Furthermore, the increasing utilization of multi-crystalline wafers for fabricating solar cells has raised the difficulty of detecting the minute micro-cracks using the foregoing conventional methods and systems.

For purposes of brevity and clarity, the description of the invention is limited hereinafter to applications related to an improved system and method for facilitating detection of micro-cracks in wafers used for fabricating solar cells. This however does not limit or preclude embodiments of the invention from other areas of application that facilitates inspection of other wafer types for defects detection. The fundamental inventive principles and concepts upon which embodiments of the invention are based shall remain common throughout the various embodiments.

An exemplary embodiment of the invention is described in greater detail hereinafter in accordance to illustrations provided in FIGS. 3 to 10 of the drawings, wherein like elements are identified with like reference numerals.

A method and apparatus for wafer inspection is described hereinafter for addressing the foregoing problems. The method and apparatus is suitable for inspecting solar wafers, as well as other wafer types such as semiconductor bare wafers or processed wafer that are used in the fabrication of integrated circuit chips.

FIG. 3 shows a flow diagram of a method 300 for inspecting a wafer, for instance a solar wafer, according to an exemplary embodiment of the invention. Defects such as micro-cracks in solar wafers typically extend between two outward facing surfaces, namely a first surface and a second surface of the solar wafer. The method 300 comprises a step 302 of directing infrared light towards the first surface of the solar wafer at an acute angle to the surface of the wafer. The first surface of the solar wafer is the lower side of the solar wafer.

The method 300 also comprises a step 304 of receiving the infrared light from a second surface of the solar wafer along a first axis, where the second surface of the solar wafer substantially outwardly opposes the first surface of the solar wafer. The second surface of a solar wafer is the upper side of the wafer.

The method 300 further comprises a step 306 of forming a first image of the second surface of the solar wafer based on infrared light received from the second surface of the wafer along the first axis.

The method yet further comprises a step 308 of receiving the infrared light from the second surface of the wafer along a second axis. In particular, the orthographic projection of the first axis on the first or second surface of the solar wafer is substantially perpendicular the orthographic projection of the second axis on the first or second surface of the solar wafer.

Alternatively, the orthographic projection of the first axis on the first or second surface of the solar wafer is substantially parallel to and coincident with the orthographic projection of the second axis on the first or second surface of the solar wafer.

The method 300 then comprises a step 310 of forming a second image of the second surface of the solar wafer based on infrared light received from the second surface of the wafer along the second axis. The method 300 then further comprises a step 312 of superposing the first and second images for obtaining a third image, wherein the third image is processable for inspecting the wafer to thereby identify defects on the solar wafer.

In accordance with an exemplary embodiment of the invention, an apparatus 100 for inspection is described with reference to FIG. 4, which shows a perspective view of the apparatus 100 according to a first embodiment of the invention. The apparatus 100 is preferably for implementing the foregoing method 300 for inspecting a solar wafer. The following description of the apparatus 100 is made with reference to an x-axis, a y-axis and a z-axis of a three-dimensional coordinate system. The x and y axes extend along a plane on which solar wafers are conveyed and are coincident therewith.

The apparatus 100 comprises a computer 102 and a first imaging device 104 and a second imaging device 106. The first and second imaging devices 104, 106 are preferably line-scan imaging cameras and are connected to the computer 102. Images captured by the first and second imaging devices 104, 106 are sent to the computer 102 for image analysis.

The apparatus 100 further comprises a light assembly that includes a first light source 108 and a second light source 110. The first and second light sources 108, 110 preferably emit infrared light that is detectable by the first and second imaging devices 104, 106. Specifically, the first and second light sources 108, 110 are positioned with respect to the first and second imaging devices 104, 106 for directing infrared light towards the first and second imaging devices 104, 106 respectively.

A conveyor system 112 is used for transporting solar wafers 114 for inspection by the apparatus 100. The conveyor system 112 has a first portion 116 and a second portion 118. The first portion 116 of the conveyor system 112 conveys a substantially planar solar wafer 114 linearly along the x-axis while the second portion 118 of the conveyor system 112 conveys the solar wafer 114 linearly along the y-axis. The solar wafer 114 is therefore conveyed substantially on the x-y plane.

More specifically, the first portion 116 of the conveyor system 112 is displaced in between the first imaging device 104 and the first light source 108 while the second portion 118 of the conveyor system 112 is displaced in between the second imaging device 106 and the second light source 110.

As the first portion 116 of the conveyor system 112 conveys the solar wafer 114 along the x-axis, the first light source 108 emits and substantially directs infrared light towards the lower surface of the solar wafer 114 at an acute angle θ. The first imaging device 104 is configured with respect to the z-axis normal to the solar wafer 114 for capturing infrared light emitted from the first light source 108 along the first axis 107. In this way, the apparatus 100 is able to capture and provide a first image of the solar wafer 114 along the x-axis.

Similarly, as the second portion 118 of the conveyor system 112 receives the solar wafer 114 from the first portion 116 and conveys the solar wafer 114 along the y-axis, the second light source 110 emits and substantially directs infrared light towards the lower surface of the solar wafer 114 at the acute angle θ. The second imaging device 106 is configured with respect to the z-axis normal to the solar wafer 114 for capturing infrared light emitted from the first light source 108 along the second axis 109. In this way, the apparatus 100 is able to capture and provide a second image of the solar wafer 114 along the y-axis. In particular, the orthographic projection of the first axis 107 on the x-y plane is substantially perpendicular the orthographic projection of the second axis 109 on the x-y plane.

With reference to FIG. 5a, the oblique arrangement of the first and second imaging devices 104, 106 with respect to the first and second light sources 108, 110, allows images captured by the apparatus 100 to show highly contrasted micro-cracks 500. FIG. 5b is an enlarged cross-sectional view of the solar wafer 114 at point B of FIG. 5a. The micro-cracks 500 extend along the x and y axes against the upper surface of the solar wafer 114.

Mathematically, the width $w_i$ of the micro-cracks 500 in the images captured by the apparatus 100 is a function of the wafer thickness $t_w$ and the acute angle θ, according to the following mathematical relationship:

$$w_i = t_w \times \sin\theta$$

For example, the solar wafer 114 typically has a thickness of 200 μm. If the acute angle θ is 30°, the width $w_i$ of the micro-cracks 500 in the images captured by the apparatus 100 is 100 μm. This advantageously increases the prominence of the micro-cracks 500 to thereby facilitate the detection of the micro-cracks 500 by the apparatus 100.

Without the use of the foregoing oblique arrangement, the micro-cracks 500 as inspected by conventional methods and devices would appear in the images having a width of 5 pixels, which is not sufficiently prominent to be detected.

Furthermore, according to the foregoing mathematical relationship, the width $w_i$ of the micro-cracks 500 contained in the images captured by the apparatus 100 is independent of the actual width of the micro-cracks 500. This means that the apparatus 100 is capable of detecting a 1 μm width micro-crack as easily as a 50 μm width micro-crack.

The pair of imaging devices 104, 106 and the pair of light sources 108, 110 preferably creates high contrasting images of the micro-cracks 500 so as to facilitate effective detection of micro-cracks 500 on the solar wafer 114 along the x and y-axes. Realistically, the micro-cracks 500 usually extend randomly in all directions.

In particular, most micro-cracks 500 generally do not extend perpendicularly to the upper and lower surfaces of the solar wafer 114. Instead, most micro-cracks 500 are angled away from the normal of the upper and lower surfaces when extending therebetween as shown in FIG. 5c.

The micro-cracks 500 preferably appear as dark lines in the images of the solar wafer 114 captured by the apparatus 100. Alternatively, the micro-cracks 500 appear as bright lines in the same images of the solar wafer 114. The apparatus 100 advantageously create high contrast images of the micro-cracks 500 to facilitate detection thereof.

FIG. 6a shows a first view 600 of the micro-crack 500 captured by the apparatus 100 when the first and second imaging devices 104, 106 are positioned perpendicularly with respect to the solar wafer 114. The micro-crack 500 is shown to have a substantially constant width. FIGS. 6b and 6c are respective second and third views of the micro-crack 500 captured by the first imaging device 104 along the x-axis and the second imaging device 106 along the y-axis.

Each of the second and third views 602, 604 shows that the micro-crack 500 therein have varying line widths along the respective crack directions. When either of the micro-crack views 602, 604 is used for inspection purposes, there is a possibility that the micro-crack 500 is not detected as a single crack but is detected as several shorter micro-cracks. In this case, the micro-crack 500 may even escape detection altogether if the micro-crack 500 changes direction too frequently and produces only segments of crack shorter than a control limit set by users of the apparatus 100.

The present invention uses a software application executable in the computer 102 to prevent the micro-crack 500 from being undetected.

Figure 7:
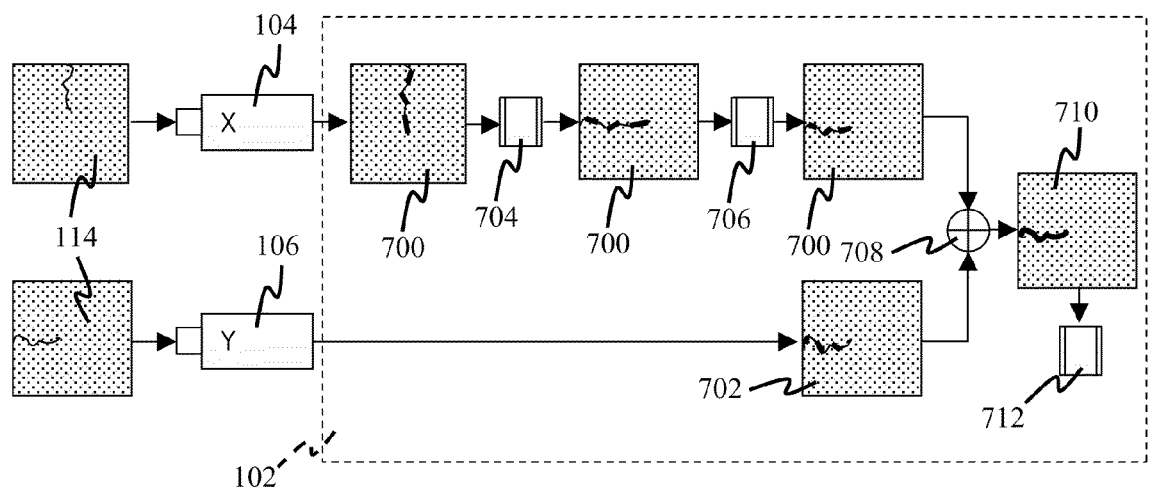
FIG. 7 shows four processes involved in processing images of micro-cracks obtained by the apparatus of FIG. 4.

As shown in FIG. 7, the first imaging device 104 obtains a first image 700 of the solar wafer 114 along the x-axis and the second imaging device 106 obtains a second image 702 of the solar wafer 114 along the y-axis. Both the first and second images 700, 702 are sent to the computer 112 where a first process 704 rotates the first image 700 relative to the second image 702 such that both images 700, 702 have the same orientation.

A second process 706 corrects the rotated first image 700 to positionally register the rotated first image 700 with the second image 702 with respect to perspective and scalar differences, and produces a corrected first image 700. In a third process 708, the corrected first image 700 and the second image 702 are superposed by an arithmetic function, such as a minimum function, to produce a final processed image 710. A fourth process 712 is then used for analysing the final processed image 710 to detect the micro-cracks 500 on the solar wafers 114. The fourth function 712 involves binarization and segmentation functions for analysing and detecting micro-cracks on the final processed image 710.

Figure 8:
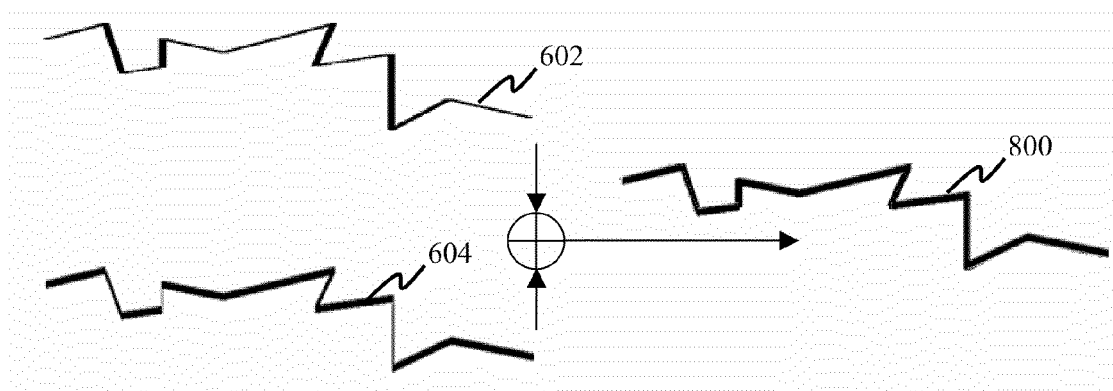
FIG. 8 shows merging of micro-cracks images obtained by the apparatus of FIG. 4.

FIG. 8 shows a micro-crack 800 in the final processed image 710, which is derived by combining the first and second views of FIGS. 6b and 6c. The micro-crack 800 appears in the final processed image 710 with uniform width and is sufficiently prominent to be detected by the image analysis process.

Figure 9:
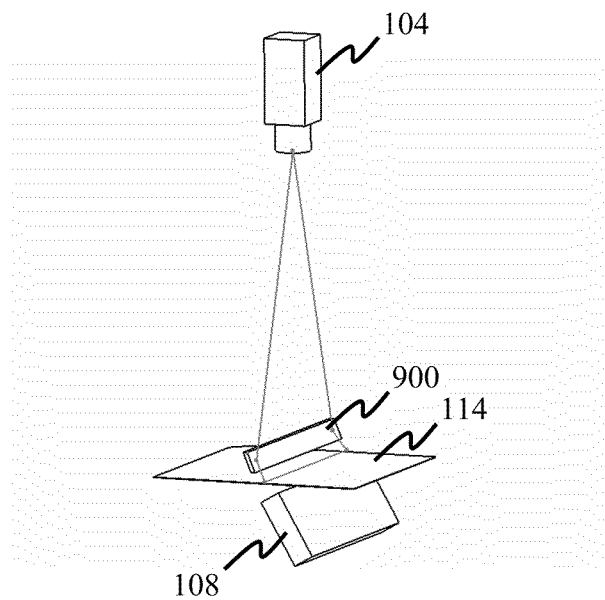
FIG. 9 shows another embodiment of the invention.

FIG. 9 shows another embodiment of the invention. An optical unit or mirror 900 is positioned adjacent to the solar wafer 114 for diverting the infrared light transmitted through the solar wafer 114 towards the first 104 or second 106 imaging device. The mirror 900 advantageously allows the first 104 or second 106 imaging device to be positioned at different angles with respect to the solar wafer 114 for receiving infrared light from the first 108 or second 110 light source via the solar wafer 114.

Figure 10:
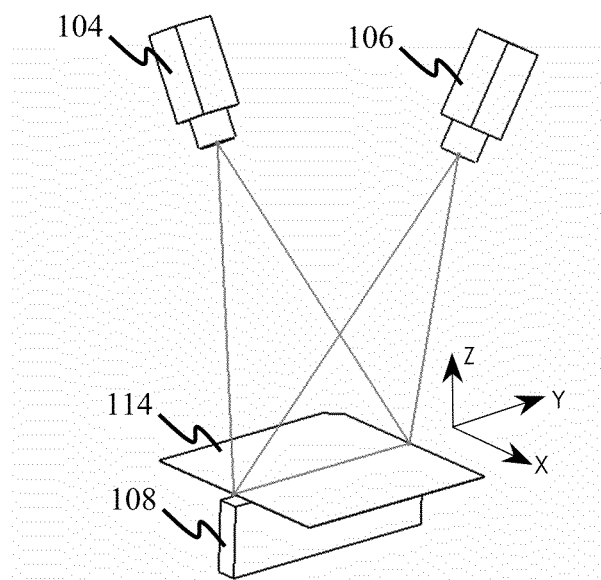
FIG. 10 shows yet another embodiment of the invention.

As shown in FIG. 10, the second imaging device 106 is relocated to a new position such that the first and second imaging devices 104, 106 share a common light source, such as the first light source 108. This arrangement is useful to fulfill certain design constrains of the apparatus 100 or due to space limitation in installing the second portion of the conveyor system 112.

Figure 11:
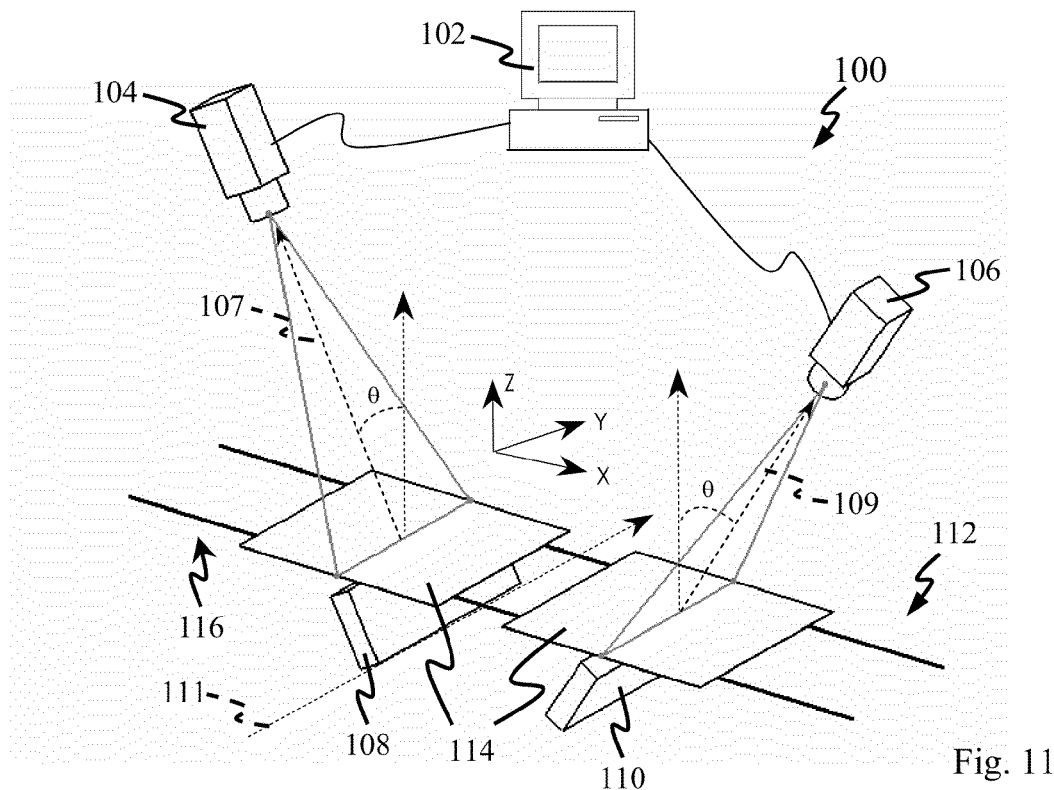
FIG. 11 shows a further embodiment of the invention.

FIG. 11 shows yet another embodiment of the invention. The second imaging device 106 and the second light source 110 are rearranged and positioned along the first portion 116 of the conveyor system 112. The first portion 116 of the conveyor system 112 is displaced in between the second imaging device 106 and the second light source 110.

More specifically, the second imaging device 106 is arranged symmetrically about a plane of symmetry (not shown) with respect to the first imaging device 104. Similarly, the second light source 110 is arranged symmetrically about the plane of symmetry with respect to the first light source 108. The plane of symmetry is parallel to the z-y plane and is perpendicular to the plane on which the solar wafer 114 is conveyed. A reference axis 111 extends along the intersection of the plane of symmetry and the plane on which the solar wafer 114 is conveyed. In this embodiment of the invention, the second portion 118 of the conveyor system 112 is not required.

Similar to the exemplary embodiment of the invention, the solar wafer 114 is transported along the x-axis. The first light source 108 emits and substantially directs infrared light along the first axis 107 towards the lower surface of the solar wafer 114 at the acute angle θ. The first imaging device 104 then captures the infrared light emanating from the upper surface of the solar wafer 114 along the first axis 107. The solar wafer 114 is displaced along the x-axis on the first portion 116 of the conveyor system 112 until the first imaging device 104 completes capture of the first image of the solar wafer 114.

Thereafter, the solar wafer 114 is displaced towards the second imaging device 106 and the second light source 110. Similarly, the second light source 110 emits and substantially directs infrared light along the second axis 109 towards the lower surface of the solar wafer 114 at the acute angle θ. The second imaging device 106 then captures the infrared light from the upper surface of the solar wafer 114 along the second axis 109.

More specifically, the first axis 107 is angled away from the second axis 109 about the reference axis 111 that extends along the plane on which the solar wafer 114 is conveyed. The orthographic projections of the first and second axes 107, 109 are substantially perpendicular to the reference axis 111.

Next, the solar wafer 114 is displaced along the x-axis on the first portion 116 of the conveyor system 112 until the second imaging device 106 completes capture of the second image of the solar wafer 114. The first and second images captured by the corresponding first and second imaging devices 104, 106 are sent to the computer 102 for image analysis using the foregoing software application to detect the micro-cracks 500.

Figure 12:
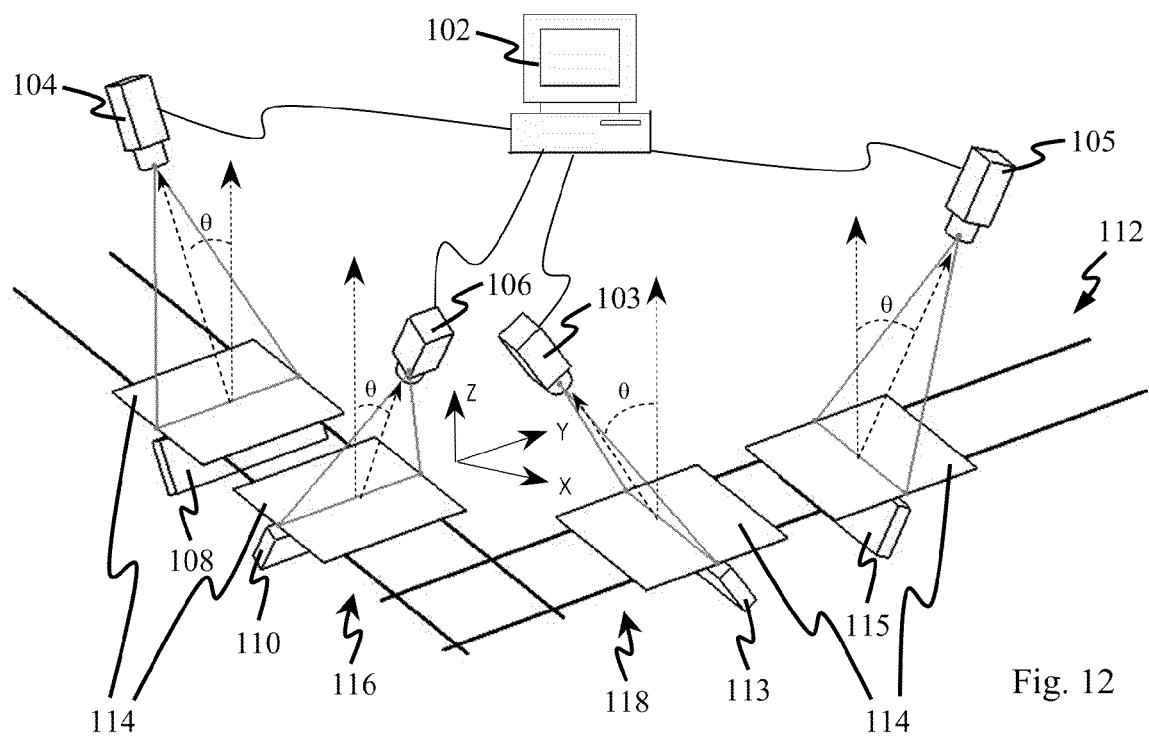
FIG. 12 shows yet another further embodiment of the invention.

In a further embodiment of the invention as shown in FIG. 12, an additional set of imaging devices and light sources is arranged on each of the first and second portions 116, 118 of the conveyor system 112. In particular, the foregoing embodiment of the invention as shown in FIG. 11 is duplicated onto the second portion 118 of the conveyor system 112 such that the apparatus 100 further comprises a third imaging device 103 and a fourth imaging device 105, as well as a third light source 113 and a fourth light source 115.

As with the foregoing embodiment of the invention as shown in FIG. 11, the solar wafer 114 first conveys along the x-axis by the first portion 116 of the conveyor system 112 for capturing the first and second images of the solar wafer 114 by the first and second imaging devices 104, 106 respectively. Thereafter, the solar wafer 114 is conveyed by the second portion 118 of the conveyor system 112 along the y-axis towards the third imaging device 103 and the third light source 113.

The third light source 113 emits and substantially directs infrared light towards the lower surface of the solar wafer 114 at the acute angle θ while the third imaging device 103 captures the infrared light from the upper surface of the solar wafer 114. The third imaging device 103 captures a third image of the solar wafer 114.

The solar wafer 114 then continues to be displaced along the y-axis on the second portion 116 of the conveyor system 112 where the fourth light source 115 emits and substantially directs infrared light towards the lower surface of the solar wafer 114 at the acute angle θ while the fourth imaging device 105 captures the infrared light from the upper surface of the solar wafer 114. The fourth imaging device 105 captures a fourth image of the solar wafer 114.

The third and fourth images together with the first and second images of the solar wafer 114 are sent to the computer 102 for image analysis using the foregoing software application for detecting the micro-cracks 500. The four images captured by the apparatus 100 advantageously allow micro-cracks of any orientation with respect to the upper and lower surfaces of the solar wafer to be substantially detected.

In the foregoing manner, an apparatus and a method for wafer inspection are described according to an exemplary embodiment of the invention for addressing the foregoing disadvantages of conventional method of performing inspection. Although only a few embodiments of the invention is disclosed, it will be apparent to one skilled in the art in view of this disclosure that numerous changes and/or modification can be made to cater to a wider range of hole sizes and heights without departing from the scope and spirit of the invention.

The invention claimed is:
1. A method for wafer inspection comprising:
directing light substantially along a first axis towards a first surface of a wafer to thereby obtain light emanating along the first axis from a second surface of the wafer, wherein the first and second surfaces of the wafer are substantially outwardly opposing and substantially extending parallel to a plane; and
directing light substantially along a second axis towards the first surface of the wafer to thereby obtain light emanating along the second axis from the second surface of the wafer, the first axis being angled away from the second axis about a reference axis extending along the plane,
wherein the orthographic projection of the first axis on the plane is substantially parallel to the orthographic projection of the second axis on the plane, and each of the orthographic projections of the first and second axes on the plane is substantially orthogonal to the reference axis.

2. The method as in claim 1, further comprising forming a first image of the first surface based on the light emanating from the second surface of the wafer substantially along the first axis, the wafer having a crack formed therein, the first image containing at least one first portion of the crack; and forming a second image of the first surface based on the light emanating from the second surface of the wafer substantially along the second axis, the second image containing at least one second portion of the crack.

3. The method as in claim 2, further comprising constructing a third image from the first and second images based on the at least one first and second portions of the crack, the third image being substantially processable for inspecting the crack in the wafer.

4. The method as in claim 3, comprising superposing the first and second images to thereby obtain the third image.

5. The method as in claim 1, wherein directing light substantially along a first axis towards a first surface of a wafer comprises directing light towards the first surface of the wafer at substantially an acute angle to the plane.

6. The method as in claim 1, wherein directing light substantially along a second axis towards a first surface of a wafer comprises directing light towards the first surface of the wafer at substantially an acute angle to the plane.

7. The method as in claim 1, wherein directing light substantially along a first axis towards a first surface of a wafer to thereby obtain the light emanating along the first axis from a second surface of the wafer comprises conveying the wafer along the orthographic projection of the first axis on the plane.

8. The method as in claim 1, wherein directing light substantially along a second axis towards the first surface of the wafer to thereby obtain light emanating along the second axis from the second surface of the wafer comprises conveying the wafer along the orthographic projection of the second axis on the plane.

9. The method as in claim 1, further comprising providing a first imaging device for capturing the light emanating along the first axis from the second surface of the wafer.

10. The method as in claim 1, further comprising providing a second imaging device for capturing the light emanating along the second axes from the second surface of the wafer.

11. An apparatus comprising:
a first light source directing light substantially along a first axis towards a first surface of a wafer to thereby obtain light emanating along the first axis from a second surface of the wafer, wherein the first and second surfaces of the wafer are substantially outwardly opposing and substantially extending parallel to a plane; and
a second light source directing light substantially along a second axis towards the first surface of the wafer to thereby obtain light emanating along the second axis from the second surface of the wafer, the first axis being angled away from the second axis about a reference axis extending along the plane,
wherein the orthographic projection of the first axis on the plane is substantially parallel to the orthographic projection of the second axis on the plane, and each of the orthographic projections of the first and second axes on the plane is substantially orthogonal to the reference axis.

12. The apparatus as in claim 11, further comprising a first imaging device for forming a first image of the first surface based on the light emanating from the second surface of the wafer substantially along the first axis, the wafer having a crack formed therein, the first image containing at least one first portion of the crack.

13. The apparatus as in claim 11, further comprising a second imaging device for forming a second image of the first surface is formed based on the light emanating from the second surface of the wafer substantially along the second axis, the second image containing at least one second portion of the crack.

14. The apparatus as in claim 11, further comprising a computer for constructing a third image from the first and second images based on the at least one first and second portions of the crack, the third image being substantially processable by the computer for inspecting the crack in the wafer.

15. The apparatus as in claim 14, wherein the computer superposes the first and second images to thereby obtain the third image.

16. The apparatus as in claim 11, wherein the first light source directs light towards the first surface of the wafer at substantially an acute angle to the plane.

17. The apparatus as in claim 11, wherein the second light source directs light towards the first surface of the wafer at substantially an acute angle to the plane.

18. The apparatus as in claim 11, further comprising a conveyer system for conveying the wafer along the orthographic projection of the first axis on the plane.

19. The apparatus as in claim 18, wherein the conveyer system conveys the wafer along the orthographic projection of the second axis on the plane.

20. The apparatus as in claim 19, wherein the orthographic projection of the first axis on the plane is substantially coincident with the orthographic projection of the second axis on the plane.

* * * * *